United States Patent
Li et al.

(10) Patent No.: US 11,753,377 B2
(45) Date of Patent: Sep. 12, 2023

(54) CRYSTAL FORM OF 2-METHYL-2-PROPANOL AND AMINO-SUBSTITUTED ARYL COMPOUND

(71) Applicant: ZHUHAI UNITED LABORATORIES CO., LTD., Guangdong (CN)

(72) Inventors: Xiaolin Li, Shanghai (CN); Chong Su, Guangdong (CN); Zhi Luo, Shanghai (CN); Fei Hao, Shanghai (CN); Peng Li, Shanghai (CN); Haiying He, Shanghai (CN); Jian Li, Shanghai (CN); Shuhui Chen, Shanghai (CN)

(73) Assignee: ZHUHAI UNITED LABORATORIES CO., LTD., Guangdong (CN)

( * ) Notice: Subject to any disclaimer, the term of this patent is extended or adjusted under 35 U.S.C. 154(b) by 0 days.

(21) Appl. No.: 18/000,685

(22) PCT Filed: Jun. 17, 2021

(86) PCT No.: PCT/CN2021/100696
§ 371 (c)(1),
(2) Date: Dec. 5, 2022

(87) PCT Pub. No.: WO2021/254456
PCT Pub. Date: Dec. 23, 2021

(65) Prior Publication Data
US 2023/0174489 A1 Jun. 8, 2023

(30) Foreign Application Priority Data
Jun. 17, 2020 (CN) .......................... 202010554402.1

(51) Int. Cl.
C07D 213/73 (2006.01)
A61P 27/00 (2006.01)

(52) U.S. Cl.
CPC ............ *C07D 213/73* (2013.01); *A61P 27/00* (2018.01); *C07B 2200/13* (2013.01)

(58) Field of Classification Search
CPC .... C07D 213/73; A61P 27/00; C07B 2200/13
See application file for complete search history.

(56) References Cited

U.S. PATENT DOCUMENTS

| 2018/0250306 A1 | 9/2018 | Brady et al. |
| 2019/0105322 A1* | 4/2019 | Macdonald ............ A61P 29/00 |
| 2022/0127243 A1 | 4/2022 | Li et al. |

FOREIGN PATENT DOCUMENTS

| CN | 108135867 A | 6/2018 |
| WO | 2019075136 A1 | 4/2019 |
| WO | 2020125659 A1 | 6/2020 |

OTHER PUBLICATIONS

Sep. 15, 2021 International Search Report issued in International Patent Application No. PCT/CN2021/100696.
Sep. 15, 2021 Written Opinion of the International Searching Authority issued in International Patent Application No. PCT/CN2021/100696.
Chinese Patent No. 2020105544021 (not published).

* cited by examiner

*Primary Examiner* — Timothy R Rozof
(74) *Attorney, Agent, or Firm* — Houston Beshining Law Office PLLC; Liangang Ye (57) ABSTRACT

A crystal form (such as formula I) of a 2-methyl-2-propanol and amino-substituted aryl compound and a preparation method therefor. Also provided is an application of the crystal form in the preparation of a medicine for treating related diseases.

14 Claims, 5 Drawing Sheets

CRYSTAL FORM OF 2-METHYL-2-PROPANOL AND AMINO-SUBSTITUTED ARYL COMPOUND

The present application is a National Stage of International Application No. PCT/CN2021/100696, filed on Jun. 17, 2021, which claims priority of the Chinese Patent Application No. CN202010554402.1 filed on Jun. 17, 2020, the contents of which are incorporated herein by reference in their entireties.

TECHNICAL FIELD

The present disclosure relates to a crystal form of a 2-methyl-2-propanol and an aryl compound substituted by amino and a preparation method therefor, further comprises a use of the crystal form in the manufacture of a medicament for treating related diseases.

BACKGROUND

Xerophthalmia, also known as keratoconjunctivitis sicca, refers to a general name of a variety of diseases that cause a decrease in tear film stability due to abnormal tear quality or amount or dynamic abnormality caused by any cause, and are accompanied by ocular discomfort (or) lesion characteristics of ocular surfaces. The specific symptoms of discomfort are manifested by eye irritation, visual disturbance, and tear film instability. The syndrome is caused by inflammation of the ocular surface, resulting in loss of lacrimal function. In addition, the syndromes are also associated with systemic autoimmunity.

Because some toxic aldehydes, such as malondialdehyde (MDA), 4-hydroxy-2-nonenal (4HNE) are produced by metabolic mechanisms of in vivo or ocular tissues and organs, these aldehydes highly react with proteins, carbohydrates, oils, and DNA, resulting in chemical modification of biomolecules and activation of inflammatory molecule regulators such as NF-kappaB, thus promoting damage to different organs, which is one of the causes of xerophthalmia.

In the present disclosure, through research, a small-molecule drug enters the ocular inflammatory site in the form of eye drops or oral administration, through a complexation reaction with aldehydes in vivo, thereby reducing aldehyde toxicity and reducing inflammation to exerting the effect of treating xerophthalmia.

CONTENT OF THE PRESENT INVENTION

The present disclosure provides a crystal form A of a compound represented by formula (I), which is characterized in that the crystal form A has an X-ray powder diffraction pattern comprising characteristic diffraction peaks at the following 2θ angles: 7.03±0.20°, 16.36±0.20°, and 21.23±0.20°.

In some embodiments of the present disclosure, the X-ray powder diffraction pattern of the crystal form A comprises characteristic diffraction peaks at the following 2θ angles: 7.03±0.20°, 8.20±0.20°, 16.36±0.20°, 17.73±0.20°, 20.69±0.20°, 21.23±0.20°, 22.51±0.20°, and 28.36±0.20°.

In some embodiments of the present disclosure, the X-ray powder diffraction pattern of the crystal form A comprises characteristic diffraction peaks at the following 2θ angles: 7.03±0.20°, 8.20±0.20°, 14.16±0.20°, 16.36±0.20°, 17.73±0.20°, 19.42±0.20°, 20.69±0.20°, 21.23±0.20°, 22.51±0.20°, and 28.36±0.20°.

In some embodiments of the present disclosure, the X-ray powder diffraction pattern of the crystal form A comprises characteristic diffraction peaks at the following 2θ angles: 7.03°, 8.20°, 9.19°, 12.53°, 13.09°, 14.16°, 15.78°, 16.36°, 17.73°, 18.46°, 19.42°, 20.15°, 20.69°, 21.23°, 22.51°, 23.45°, 24.02°, 24.86°, 27.36°, 28.36°, 31.36°, 32.41°, and 38.61°.

Figure 1:
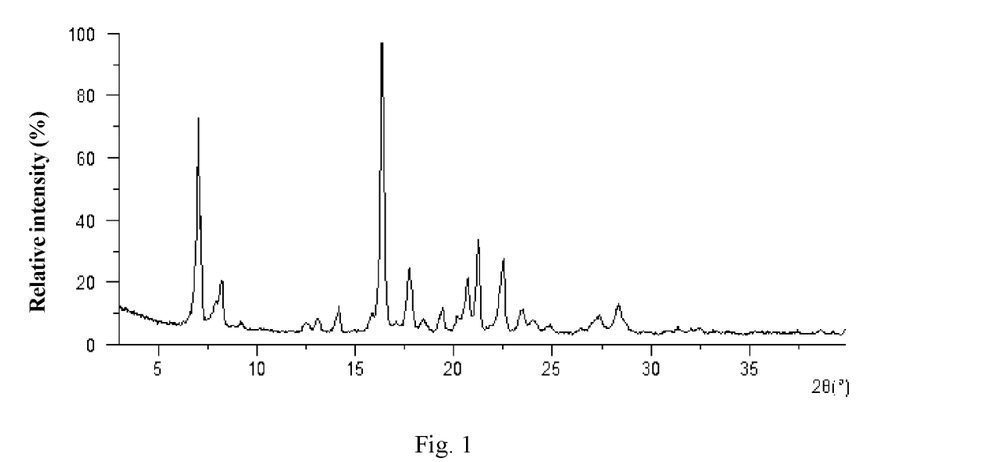
FIG. 1 is the XRPD pattern of the crystal form A of the compound represented by formula (I) measured by Cu-Kα radiation.

In some embodiments of the present disclosure, the crystal form A has an XRPD pattern as shown in FIG. 1.

In some embodiments of the present disclosure, the crystal form A has analytical data of the XRPD pattern as shown in Table 1.

TABLE 1

Analytical data of the XRPD pattern of the crystal form A of the compound represented by formula (I)

| No. | 2θ Angle (°) | d-Spacing (Å) | Relative intensity (%) |
|---|---|---|---|
| 1 | 7.03 | 12.57 | 65.26 |
| 2 | 8.20 | 10.78 | 16.16 |
| 3 | 9.19 | 9.62 | 2.00 |
| 4 | 12.53 | 7.06 | 2.88 |
| 5 | 13.09 | 6.76 | 4.75 |
| 6 | 14.16 | 6.25 | 8.77 |
| 7 | 15.78 | 5.62 | 5.44 |
| 8 | 16.36 | 5.42 | 100.00 |
| 9 | 17.73 | 5.00 | 21.40 |
| 10 | 18.46 | 4.81 | 4.47 |
| 11 | 19.42 | 4.57 | 8.32 |
| 12 | 20.15 | 4.41 | 5.59 |
| 13 | 20.69 | 4.29 | 18.96 |
| 14 | 21.23 | 4.19 | 32.85 |
| 15 | 22.51 | 3.95 | 25.45 |
| 16 | 23.45 | 3.79 | 7.80 |
| 17 | 24.02 | 3.70 | 4.11 |
| 18 | 24.86 | 3.58 | 2.51 |
| 19 | 27.36 | 3.26 | 5.73 |
| 20 | 28.36 | 3.15 | 9.71 |
| 21 | 31.36 | 2.85 | 1.98 |
| 22 | 32.41 | 2.76 | 1.58 |
| 23 | 38.61 | 2.33 | 0.96 |

The present disclosure provides a crystal form B of the compound represented by formula (I), which is characterized in that the crystal form B has an X-ray powder diffraction pattern comprising characteristic diffraction peaks at the following 2θ angles: 14.28±0.20°, 14.78±0.20°, and 20.18±0.20°.

(I)

(I)

In some embodiments of the present disclosure, the X-ray powder diffraction pattern of the crystal form B comprises characteristic diffraction peaks at the following 2θ angles: 10.08±0.20°, 12.60±0.20°, 14.28±0.20°, 14.78±0.20°, 20.18±0.20°, 21.32±0.20°, 26.08±0.20°, and 27.69±0.20°.

In some embodiments of the present disclosure, the X-ray powder diffraction pattern of the crystal form B comprises characteristic diffraction peaks at the following 2θ angles: 10.08±0.20°, 12.60±0.20°, 14.28±0.20°, 14.78±0.20°, 20.18±0.20°, 21.32±0.20°, 25.26±0.20°, 26.08±0.20°, 27.69±0.20°, and 29.63±0.20°.

In some embodiments of the present disclosure, the X-ray powder diffraction pattern of the crystal form B comprises characteristic diffraction peaks at the following 2θ angles: 8.09°, 10.08°, 12.60°, 14.28°, 14.78°, 15.13°, 16.08°, 16.38°, 17.51°, 18.25°, 20.18°, 20.56°, 21.12°, 21.32°, 22.65°, 23.85°, 24.15°, 24.77°, 25.26°, 26.08°, 26.34°, 26.64°, 27.69°, 28.94°, 29.12°, 29.63°, 30.43°, 32.16°, 32.53°, 33.34°, 33.74°, 34.74°, 35.13°, 36.20°, 37.95°, and 38.24°.

Figure 2:
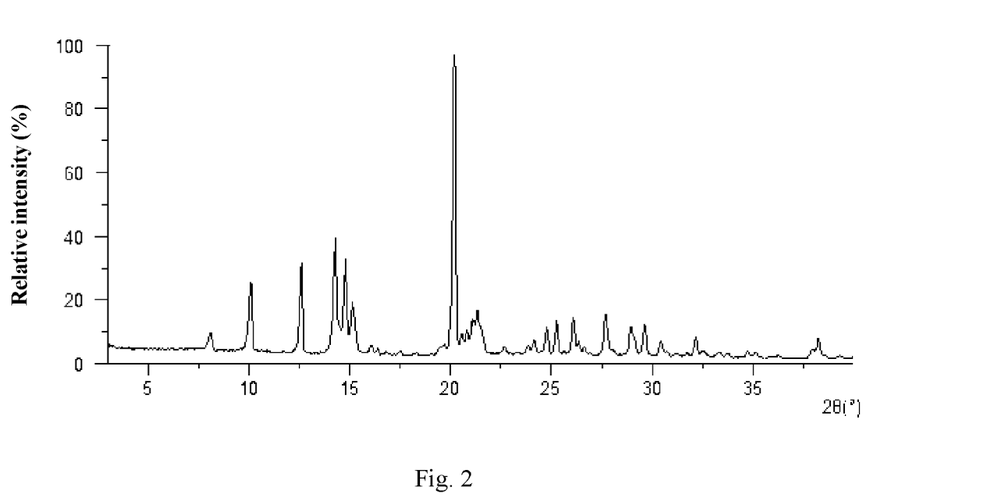
FIG. 2 is the XRPD pattern of the crystal form B of the compound represented by formula (I) measured by Cu-Kα radiation.

In some embodiments of the present disclosure, the crystal form B has an XRPD pattern as shown in FIG. 2.

In some embodiments of the present disclosure, the crystal form B has analytical data of the XRPD pattern as shown in Table 2.

TABLE 2

Analytical data of the XRPD pattern of the crystal form B of the compound represented by formula (I)

| No. | 2θ Angle (°) | d-Spacing (Å) | Relative intensity (%) |
|---|---|---|---|
| 1 | 8.09 | 10.93 | 5.84 |
| 2 | 10.08 | 8.77 | 22.96 |
| 3 | 12.60 | 7.03 | 29.57 |
| 4 | 14.28 | 6.20 | 36.44 |
| 5 | 14.78 | 5.99 | 30.10 |
| 6 | 15.13 | 5.86 | 17.33 |
| 7 | 16.08 | 5.51 | 3.30 |
| 8 | 16.38 | 5.41 | 1.91 |
| 9 | 17.51 | 5.07 | 1.23 |
| 10 | 18.25 | 4.86 | 0.59 |
| 11 | 20.18 | 4.40 | 100.00 |
| 12 | 20.56 | 4.32 | 7.21 |
| 13 | 21.12 | 4.21 | 12.26 |
| 14 | 21.32 | 4.17 | 14.60 |
| 15 | 22.65 | 3.93 | 3.09 |
| 16 | 23.85 | 3.73 | 3.59 |
| 17 | 24.15 | 3.69 | 5.62 |
| 18 | 24.77 | 3.59 | 9.63 |
| 19 | 25.26 | 3.53 | 11.70 |
| 20 | 26.08 | 3.42 | 12.94 |
| 21 | 26.34 | 3.38 | 4.84 |
| 22 | 26.64 | 3.35 | 3.11 |
| 23 | 27.69 | 3.22 | 14.23 |
| 24 | 28.94 | 3.09 | 10.26 |
| 25 | 29.12 | 3.07 | 6.58 |
| 26 | 29.63 | 3.02 | 10.98 |
| 27 | 30.43 | 2.94 | 5.15 |
| 28 | 32.16 | 2.78 | 6.44 |
| 29 | 32.53 | 2.75 | 2.18 |
| 30 | 33.34 | 2.69 | 1.73 |
| 31 | 33.74 | 2.66 | 1.38 |
| 32 | 34.74 | 2.58 | 2.56 |
| 33 | 35.13 | 2.55 | 2.06 |
| 34 | 36.20 | 2.48 | 0.92 |
| 35 | 37.95 | 2.37 | 2.77 |
| 36 | 38.24 | 2.35 | 6.40 |

In some embodiments of the present disclosure, the crystal form B has a differential scanning calorimetry curve with a peak value of an endothermic peak at 183.85±3.0° C.

Figure 7:
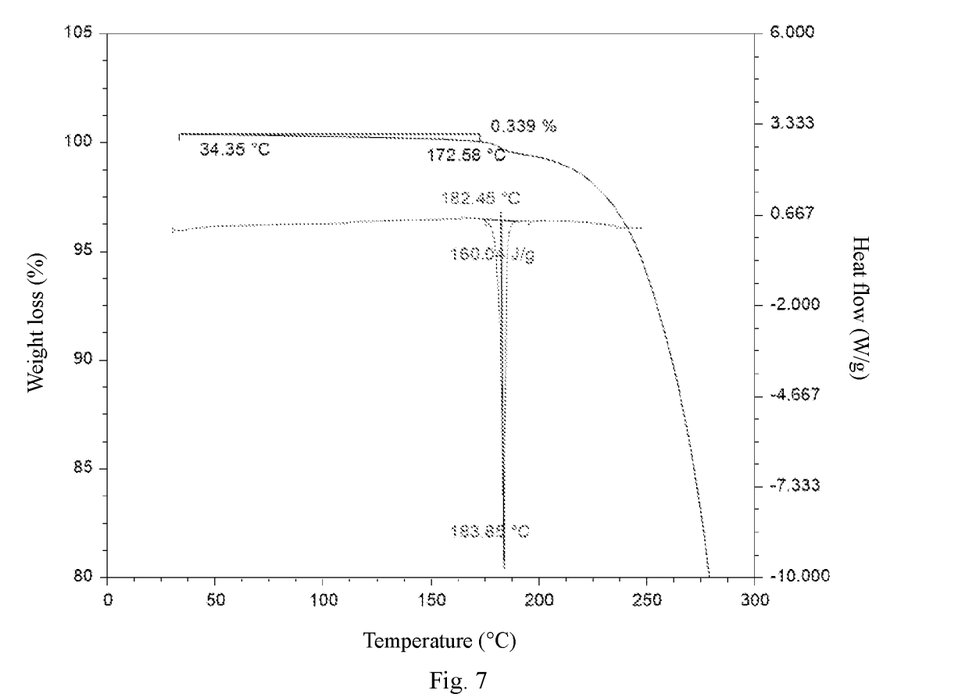
FIG. 7 is the DSC and TGA pattern of the crystal form B of the compound represented by formula (I)

In some embodiments of the present disclosure, the crystal form B has a DSC pattern as shown in FIG. 7.

In some embodiments of the present disclosure, the crystal form B has a thermogravimetric analysis curve with a weight loss of 0.339% occurred at 172.58° C.±3.0° C.

In some embodiments of the present disclosure, the crystal form B has a TGA pattern as shown in FIG. 7.

The present disclosure provides a crystal form C of the compound represented by formula (I), which is characterized in that the crystal form C has an X-ray powder diffraction pattern comprising characteristic diffraction peaks at the following 2θ angles: 11.91±0.20°, 18.36±0.20°, and 19.46±0.20°.

(I)

In some embodiments of the present disclosure, the X-ray powder diffraction pattern of the crystal form C comprises characteristic diffraction peaks at the following 2θ angles: 5.97±0.20°, 10.66±0.20°, 11.91±0.20°, 16.09±0.20°, 18.36±0.20°, 19.46±0.20°, 19.89±0.20°, and 23.99±0.20°.

In some embodiments of the present disclosure, the X-ray powder diffraction pattern of the crystal form C comprises characteristic diffraction peaks at the following 2θ angles: 5.97±0.20°, 10.66±0.20°, 11.91±0.20°, 12.65±0.20°, 16.09±0.20°, 18.36±0.20°, 19.46±0.20°, 19.89±0.20°, 23.99±0.20°, and 25.47±0.20°.

In some embodiments of the present disclosure, the X-ray powder diffraction pattern of the crystal form C comprises characteristic diffraction peaks at the following 2θ angles: 5.97°, 10.66°, 11.91°, 12.65°, 14.06°, 14.82°, 15.73°, 16.09°, 17.82°, 18.36°, 19.46°, 19.89°, 20.16°, 20.82°, 21.35°, 21.93°, 23.99°, 25.47°, 26.42°, 27.33°, 28.24°, 29.26°, 31.26°, 31.96°, 32.31°, 32.69°, 33.19°, 33.79°, 34.93°, 35.48°, 36.05°, 36.74°, 37.78°, 38.57°, and 39.32°.

Figure 3:
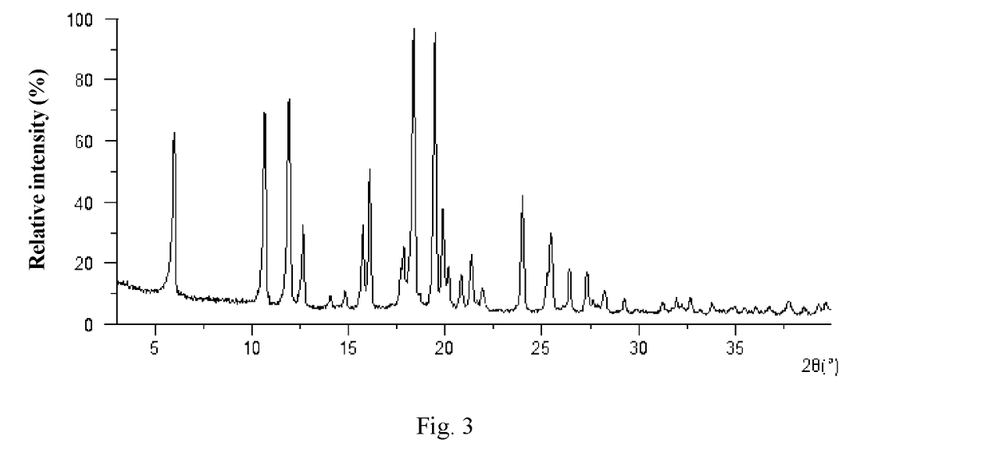
FIG. 3 is the XRPD pattern of the crystal form C of the compound represented by formula (I) measured by Cu-Kα radiation.

In some embodiments of the present disclosure, the crystal form C has an XRPD pattern as shown in FIG. 3.

In some embodiments of the present disclosure, the crystal form C has analytical data of the XRPD pattern as shown in Table 3.

TABLE 3

Analytical data of the XRPD pattern of the crystal form C of the compound represented by formula (I)

| No. | 2θ Angle (°) | d-Spacing (Å) | Relative intensity (%) |
|---|---|---|---|
| 1 | 5.97 | 14.80 | 57.24 |
| 2 | 10.66 | 8.30 | 67.66 |
| 3 | 11.91 | 7.43 | 72.59 |
| 4 | 12.65 | 7.00 | 27.70 |
| 5 | 14.06 | 6.30 | 4.31 |
| 6 | 14.82 | 5.98 | 5.86 |
| 7 | 15.73 | 5.64 | 29.17 |
| 8 | 16.09 | 5.51 | 49.71 |
| 9 | 17.82 | 4.98 | 20.18 |
| 10 | 18.36 | 4.83 | 100.00 |
| 11 | 19.46 | 4.56 | 98.40 |
| 12 | 19.89 | 4.46 | 35.44 |

TABLE 3-continued

Analytical data of the XRPD pattern of the crystal form C of the compound represented by formula (I)

| No. | 2θ Angle (°) | d-Spacing (Å) | Relative intensity (%) |
|---|---|---|---|
| 13 | 20.16 | 4.41 | 14.94 |
| 14 | 20.82 | 4.27 | 12.28 |
| 15 | 21.35 | 4.16 | 19.94 |
| 16 | 21.93 | 4.05 | 7.41 |
| 17 | 23.99 | 3.71 | 41.26 |
| 18 | 25.47 | 3.50 | 27.06 |
| 19 | 26.42 | 3.37 | 15.02 |
| 20 | 27.33 | 3.26 | 13.96 |
| 21 | 28.24 | 3.16 | 7.34 |
| 22 | 29.26 | 3.05 | 4.20 |
| 23 | 31.26 | 2.86 | 3.34 |
| 24 | 31.96 | 2.80 | 5.46 |
| 25 | 32.31 | 2.77 | 1.39 |
| 26 | 32.69 | 2.74 | 5.17 |
| 27 | 33.19 | 2.70 | 1.34 |
| 28 | 33.79 | 2.65 | 3.35 |
| 29 | 34.93 | 2.57 | 2.09 |
| 30 | 35.48 | 2.53 | 1.80 |
| 31 | 36.05 | 2.49 | 1.87 |
| 32 | 36.74 | 2.45 | 1.90 |
| 33 | 37.78 | 2.38 | 4.27 |
| 34 | 38.57 | 2.33 | 1.82 |
| 35 | 39.32 | 2.29 | 2.90 |

The present disclosure provides a crystal form D of a compound represented by formula (II), which is characterized in that the crystal form D has an X-ray powder diffraction pattern comprising characteristic diffraction peaks at the following 2θ angles: 7.020±0.200°, 16.243±0.200°, and 17.690±0.200°.

(II)

In some embodiments of the present disclosure, the X-ray powder diffraction pattern of the crystal form D comprises characteristic diffraction peaks at the following 2θ angles: 7.020±0.200°, 8.131±0.200°, 16.243±0.200°, 17.690±0.200°, and 21.081±0.200°.

In some embodiments of the present disclosure, the X-ray powder diffraction pattern of the crystal form D comprises characteristic diffraction peaks at the following 2θ angles: 7.020±0.200°, 8.131±0.200°, 14.029±0.200°, 16.243±0.200°, 17.690±0.200°, 21.081±0.200°, and 22.286±0.200°.

In some embodiments of the present disclosure, the X-ray powder diffraction pattern of the crystal form D comprises characteristic diffraction peaks at the following 2θ angles: 7.020±0.200°, 8.131±0.200°, 12.461±0.200°, 14.029±0.200°, 16.243±0.200°, 17.690±0.200°, 20.549±0.200°, 21.081±0.200°, and 22.286±0.200°.

In some embodiments of the present disclosure, the X-ray powder diffraction pattern of the crystal form D comprises characteristic diffraction peaks at the following 2θ angles: 7.020°, 7.840°, 8.131°, 9.190°, 12.461°, 13.031°, 14.029°, 15.669°, 16.243°, 16.977°, 17.690°, 18.401°, 19.279°, 20.549°, 21.081°, 22.286°, 23.364°, 23.918°, 24.716°, 27.126°, and 28.209°.

Figure 8:
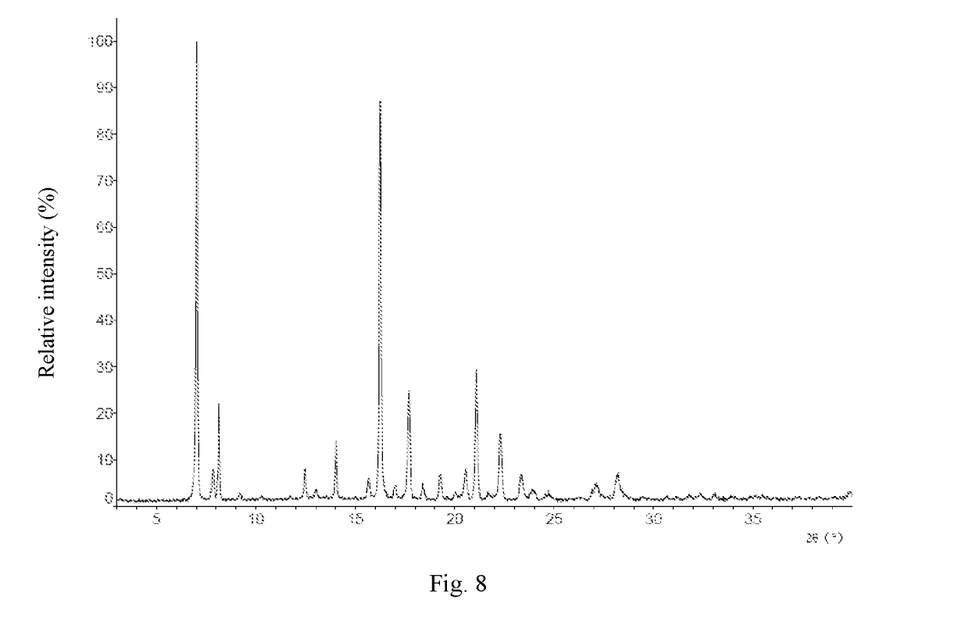
FIG. 8 is the XRPD pattern of the crystal form D of the compound represented by formula (II) measured by Cu-Kα radiation.

In some embodiments of the present disclosure, the crystal form D has an XRPD pattern as shown in FIG. 8.

In some embodiments of the present disclosure, the crystal form D has analytical data of the XRPD pattern as shown in Table 4.

TABLE 4

Analytical data of the XRPD pattern of the crystal form D of the compound represented by formula (II)

| No. | 2θ Angle (°) | d-Spacing (Å) | Relative intensity (%) |
|---|---|---|---|
| 1 | 7.020 | 12.5809 | 100.0 |
| 2 | 7.840 | 11.2669 | 6.6 |
| 3 | 8.131 | 10.8643 | 20.8 |
| 4 | 9.190 | 9.6152 | 1.7 |
| 5 | 12.461 | 7.0977 | 6.6 |
| 6 | 13.031 | 6.7885 | 2.4 |
| 7 | 14.029 | 6.3074 | 12.6 |
| 8 | 15.669 | 5.6510 | 4.3 |
| 9 | 16.243 | 5.4526 | 86.7 |
| 10 | 16.977 | 5.2184 | 2.4 |
| 11 | 17.690 | 5.0095 | 23.2 |
| 12 | 18.401 | 4.8175 | 3.6 |
| 13 | 19.279 | 4.6001 | 5.2 |
| 14 | 20.549 | 4.3185 | 6.5 |
| 15 | 21.081 | 4.2107 | 27.9 |
| 16 | 22.286 | 3.9857 | 14.2 |
| 17 | 23.364 | 3.8042 | 5.4 |
| 18 | 23.918 | 3.7173 | 2.1 |
| 19 | 24.716 | 3.5991 | 1.9 |
| 20 | 27.126 | 3.2846 | 3.5 |
| 21 | 28.209 | 3.1609 | 5.7 |

In some embodiments of the present disclosure, the crystal form D has a differential scanning calorimetry curve with a peak value of an endothermic peak at 99.8±3.0° C. and 181.97.0±3.0° C., respectively.

Figure 9:
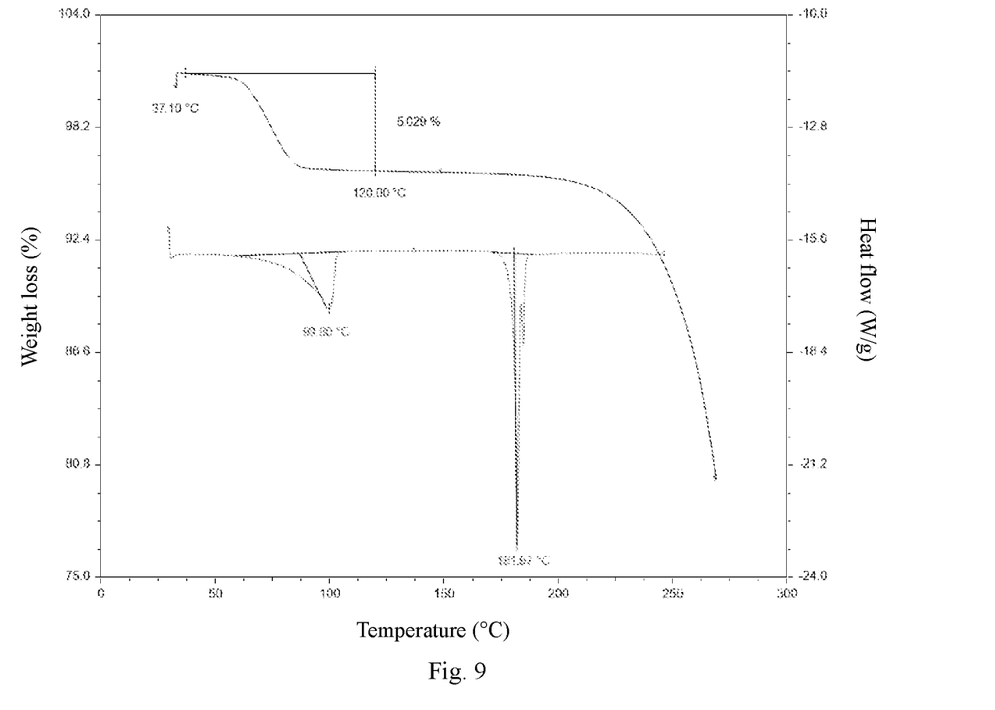
FIG. 9 is the DSC and TGA pattern of the crystal form D of the compound represented by formula (II).

In some embodiments of the present disclosure, the crystal form D has a DSC pattern as shown in FIG. 9.

In some embodiments of the present disclosure, the crystal form D has a thermogravimetric analysis curve with a weight loss of 5.029% occurred at 120.0° C.±3.0° C.

In some embodiments of the present disclosure, the crystal form D has a TGA pattern as shown in FIG. 9.

The present disclosure also provides a use of the crystal form A, the crystal form B and the crystal form C in the manufacture of a medicament for treating diseases related to an aldehyde trapping agent.

The present disclosure also provides a use of the crystal form A, the crystal form B, the crystal form C and the crystal form D in the manufacture of a medicament for treating diseases related to an aldehyde trapping agent.

In some embodiments of the present disclosure, the use is characterized in that the medicament for treating diseases related to the aldehyde trapping agent is a medicament for treating xerophthalmia.

Definition and Description

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known to those skilled in the art. Preferred embodiments include, but are not limited to, the embodiments of the present disclosure.

The chemical reactions of the embodiments of the present disclosure are carried out in a suitable solvent, and the solvent should be suitable for the chemical change of the present disclosure, and the reagents and materials required. In order to obtain the compounds of the present disclosure, it is sometimes necessary for those skilled in the art to modify or select the synthetic steps or reaction schemes based on the existing embodiments.

The present disclosure will be specifically described below by way of embodiments, but the scope of the present disclosure is not limited thereto.

All solvents used in the present disclosure are commercially available and can be directly used without further purification.

The solvents used in the present disclosure are commercially available. The following abbreviations are used in the present disclosure: DCM represents dichloromethane; DMF represents N,N-dimethylformamide; DMSO represents dimethyl sulfoxide; EtOH represents ethanol; MeOH represents methanol; TFA represents trifluoroacetic acid; ATP represents adenosine triphosphate; HEPES represents 4-hydroxyethylpiperazine ethane sulfonic acid; $MgCl_2$ represents magnesium dichloride.

Technical Effect

The crystal form of the compound of the present disclosure has good stability and is easy to be made into drugs; the compound of the present disclosure has a better aldehyde complexing capacity, high safety and low possibility of drug interaction; the compound of the present disclosure has good pharmacokinetic characteristics and is helpful to alleviate eye inflammation thereby achieving the purpose of treating xerophthalmia.

X-Ray Powder Diffractometer (XRPD) Method in the Present Disclosure

Instrument model: X'Pert3 X-ray diffractometer from PANalytical

Detection method: Approximately 10 mg of the sample was used for XRPD detection.

Detailed XRPD parameters are as follows:

Radiation source: Cu, Kα (Kα1 (Å): 1.540598, Kα2 (Å): 1.544426; Kα2/Kα1 intensity ratio: 0.50)
Voltage: 45 kilovolts (kV)
Current: 40 milliamps (mA)
Divergent slit: 1/16 deg
Scan mode: continuous
Scanning range: from 3.0 to 40.0 deg
Scanning time per step: 46.665 seconds
Step size: 0.0263 deg

DETAILED DESCRIPTION OF THE PREFERRED EMBODIMENT

In order to better understand the contents of the present disclosure, the content of the present disclosure will be further described below with reference to specific embodiments, but the specific embodiments are not intended to limit the content of the present disclosure.

Embodiment 1: Preparation of the Compound Represented by Formula (I)

Compound represented by formula (I)

Synthetic Route:

Step 1: Synthesis of Compound 1-2

Bis(pinacolato)diboron (3.65 g, 14.39 mmol, 2 eq), Pd(dppf)Cl$_2$ (526.35 mg, 719.34 μmol, 0.1 eq) and potassium acetate (1.41 g, 14.39 mmol, 2 eq) were added to a solution of compound 1-1 (2 g, 7.19 mmol, 1 eq) in toluene (30 mL), and then the reaction mixture was reacted at 110° C. for 3 hours. After the reaction was completed, the reaction solution was concentrated under reduced pressure to obtain crude product 1-2.

Step 2: Synthesis of Compound 1-4

Compound 1-3 (2.3 g, 7.07 mmol, 1 eq), cesium carbonate (4.61 g, 14.14 mmol, 2 eq) and Pd(dppf)Cl$_2$ (517.32 mg, 707.00 μmol, 0.1 eq) were added to a solution of compound 1-2 (1.63 g, 7.07 mmol, 1 eq) in toluene (50 mL) and water (10 mL), and then the reaction mixture was reacted at 110° C. under nitrogen atmosphere for 6 hours. After the reaction was completed, the reaction solution was filtered with diatomite, and the filtrate was concentrated under reduced pressure to obtain a crude product. The crude product was separated by silica gel column chromatography (SiO$_2$, petroleum ether/ethyl acetate=5:1-0:1). Compound 1-4 was obtained. LCMS: 350.1 [M+1]$^+$.

Step 3: Synthesis of Compound 1-5

Pd/C (1.7 g, 5% purity) was added to a solution of compound 1-4 (1.58 g, 4.52 mmol, 1 eq) in methanol (50 mL) and ethyl acetate (50 mL), and then the reaction mixture was reacted at 20° C. for 3 hours at 15 psi under hydrogen atmosphere. After the reaction was completed, the reaction solution was filtered with diatomite, and the filtrate was concentrated under reduced pressure to obtain compound 1-5. LCMS: 320 [M+1]$^+$; $^1$H NMR (400 MHz, DMSO-d$_6$) δ ppm 7.96 (t, J=1.76 Hz, 1H), 7.54 (d, J=11.84 Hz, 1H), 7.39 (s, 1H), 6.95 (d, J=6.58 Hz, 1H), 6.82 (s, 2H), 6.66 (s, 2H), 3.83 (d, J=3.96 Hz, 6H).

Step 4: Synthesis of the Compound Represented by Formula (I)

Methylmagnesium bromide (3 M, 31.32 mL, 20 eq) was added to a solution of compound 1-5 (1.5 g, 4.70 mmol, 1 eq) in tetrahydrofuran (150 mL) at 0° C., and the reaction mixture was reacted at 20° C. for 3 hours. After the reaction was completed, the reaction solution was poured into saturated ammonium chloride solution, added with 50 mL of ethyl acetate to separate the phases. The aqueous phase was extracted with ethyl acetate (50 mL*3), and the organic phases were combined, dried over anhydrous sodium sulfate, and filtered, concentrated under reduced pressure to obtain a crude product. The crude product was separated by HPLC (column type: Xtimate C18 150*25 mm*5 μm; mobile phase: [water (10 mM ammonium bicarbonate solution)-acetonitrile]; B (acetonitrile) %: 25%-45%, 10.5 min). The compound represented by formula (I) was obtained. LCMS: 320.0[M+1]$^+$; $^1$H NMR (400 MHz, DMSO-d$_6$) δ ppm 7.77 (s, 1H), 7.05 (s, 1H), 6.91 (d, J=12.28 Hz, 1H), 6.67 (d, J=7.46 Hz, 1H), 5.63 (s, 2H), 5.27-5.48 (m, 4H), 1.51 (s, 12H).

In some embodiments of the present disclosure, the compound represented by formula (I) could also be prepared by the following route:

Compound represented by formula (I)

Step 1: Preparation of Compound 2

After compound 1 (100 g, 460.79 mmol, 1 eq) was dissolved in absolute ethanol (1 L), concentrated sulfuric acid (225.97 g, 2.30 mol, 122.81 mL, 5 eq) and anhydrous sodium sulfate $Na_2SO_4$ (65.45 g, 460.79 mmol, 46.75 mL, 1 eq) were added thereto, and the reaction solution was stirred at 85° C. for 48 hours. After the reaction was completed, the reaction solution was cooled to room temperature. The saturated sodium bicarbonate aqueous solution (1 L) was added dropwise to the reaction solution. A large amount of solid was formed, filtered, and the filter cake was washed with water (500 mL), and the resulting solid was vacuum-dried to obtain compound 2.

$^1$H NMR (400 MHz, $CDCl_3$) δ 8.10 (d, J=1.8 Hz, 1H), 7.26 (s, 1H), 4.47 (q, J=7.1 Hz, 2H), 1.46 (t, J=7.2 Hz, 3H).

Step 2: Preparation of Compound 3

Compound 2 (70.00 g, 285.63 mmol, 1 eq) was dissolved in tetrahydrofuran (1 L), cooled to −78° C. under nitrogen protection, and methyllithium (1.6 M, 892.59 mL, 5 eq) was slowly added dropwise to the reaction solution, and the reaction solution was stirred at −78° C. for 3 hours. After the reaction was completed, the reaction was quenched by adding dropwise with water (100 mL), raised to room temperature, diluted with saturated ammonium chloride aqueous solution (500 mL), and extracted with ethyl acetate (500 mL*3). The organic phases were combined, dried over anhydrous sodium sulfate, and concentrated under reduced pressure to obtain a crude product. The crude product was slurried with n-heptane (500 mL), filtered, and dried to obtain compound 3.

$^1$H NMR (400 MHz, $CDCl_3$) δ 7.86 (d, J=1.9 Hz, 1H), 6.98 (d, J=1.9 Hz, 1H), 4.57 (br s, 2H), 1.57 (s, 6H).

Step 3: Preparation of Compound 5

Compound 4 (50 g, 189.39 mmol, 1 eq) was dissolved in ethanol (500 mL), then concentrated sulfuric acid (92.88 g, 946.95 mmol, 50.48 mL, 5 eq) and anhydrous sodium sulfate (26.90 g, 189.39 mmol, 1 eq) were added thereto, and the reaction solution was stirred at 85° C. for 72 hours. After the reaction was completed, the reaction solution was slowly poured into sodium carbonate aqueous solution (200 g of sodium carbonate dissolved in 5 L of water) at 10° C., stirred at this temperature for 1 hour, filtered, and the filter cake was washed with water (1 L). The resulting solid was vacuum-dried (15° C.) to obtain compound 5.

$^1$H NMR (400 MHz, $CDCl_3$) δ 8.22 (d, J=6.0 Hz, 1H), 7.49 (d, J=7.5 Hz, 1H), 4.43 (q, J=7.4 Hz, 2H), 1.39 (t, J=7.3 Hz, 3H).

Step 4: Preparation of Compound 6

Compound 5 (20 g, 68.48 mmol, 1 eq), bis(pinacolato)diboron (34.78 g, 136.96 mmol, 2 eq), [1,1-bis(diphenylphosphino)ferrocene] palladium(II)dichloride dichloromethane adduct (5.59 g, 6.85 mmol, 0.1 eq) and potassium acetate (13.44 g, 136.95 mmol, 2 eq) were added to dioxane (250 mL), and then the system was replaced with nitrogen for three times, and the reaction solution was stirred at 90° C. for 4 hours. After the reaction was completed, the reaction solution was filtered with diatomite, and the filtrate was concentrated, and the residue was chromatographed by column chromatography (petroleum ether:ethyl acetate=10:1 to 2:1) to obtain a crude product of the compound. The crude product was slurried with n-heptane (100 mL), stirred at 15° C. for 12 hours, filtered, and the filter cake was dried to obtain compound 6.

$^1$H NMR (400 MHz, $CDCl_3$) δ 8.39 (d, J=5.0 Hz, 1H), 7.35 (d, J=8.0 Hz, 1H), 4.43 (q, J=7.0 Hz, 2H), 1.42-1.38 (m, 15H).

Step 5: Preparation of Compound 7

Compound 6 (15 g, 44.23 mmol, 1 eq), compound 3 (11.25 g, 48.68 mmol, 1.1 eq), [1,1-bis(diphenylphosphino)ferrocene] palladium(II)dichloride dichloromethane adduct (3.63 g, 4.45 mmol, 0.1 eq) and cesium carbonate (43.23 g, 132.70 mmol, 3 eq) were added to dioxane (50 mL) and water (30 mL), and then the system was replaced with nitrogen for three times, and the reaction solution was stirred at 90° C. for 12 hours. After the reaction was completed, the reaction solution was diluted with ethyl acetate (500 mL) and filtered through diatomite. The filtrate was washed with saturated brine (200 mL), and the organic phase was concentrated, and the residue was chromatographed by column chromatography (petroleum ether:ethyl acetate=4:1) to obtain a crude product of the compound. The crude product was slurried with n-heptane (150 mL), stirred at 15° C. for 12 hours, filtered, and the filter cake was dried to obtain compound 7.

$^1$H NMR (400 MHz, $CDCl_3$) δ 8.13 (s, 1H), 8.08 (d, J=6.5 Hz, 1H), 7.53 (d, J=9.5 Hz, 1H), 7.12 (s, 1H), 4.77 (br s, 2H), 4.45 (q, J=7.0 Hz, 2H), 2.85 (br s, 1H), 1.74 (s, 6H), 1.41 (t, J=7.0 Hz, 3H).

Step 6: Preparation of Compound 8

Compound 7 (4.2 g, 11.56 mmol, 1 eq) was dissolved in tetrahydrofuran (250 mL), and the system was protected with nitrogen, then wet Pd/C (5 g, 10% of content) was added thereto, and the gas was replaced by hydrogen balloon (15 psi) for three times, and the mixture was stirred at 15° C. for 4 hours. After the reaction was completed, the reaction solution was filtered through diatomite. The filtrate was directly evaporated to dryness by rotary evaporation to obtain compound 8.

$^1$H NMR (400 MHz, DMSO-$d_6$) δ 7.87-7.77 (m, 1H), 7.51 (d, J=11.5 Hz, 1H), 7.10 (s, 1H), 6.87 (d, J=7.0 Hz, 1H), 6.60 (s, 2H), 5.72 (s, 2H), 5.51 (s, 1H), 4.28 (q, J=7.4 Hz, 2H), 1.52 (s, 6H), 1.32 (t, J=7.4 Hz, 3H).

Step 7: Preparation of the Compound Represented by Formula (I)

Compound 8 (3.8 g, 11.40 mmol, 1 eq) was dissolved in tetrahydrofuran (80 mL), and cooled to 0° C. under nitrogen protection. Methylmagnesium bromide (3 M, 75.99 mL, 20 eq) was added dropwise to the reaction solution, and the reaction solution was stirred at 0° C. for 2 hours. After the reaction was completed, the reaction was quenched slowly with water (100 mL), and then diluted with saturated ammonium chloride aqueous solution (100 mL). After the completion of dilution, the mixture was extracted with ethyl acetate (200 mL*3), and the organic phase was concentrated under reduced pressure, and the residue was chromatographed by column chromatography (petroleum ether:ethyl acetate=2:1 to 1:1) to obtain the compound represented by formula (I).

$^1$H NMR (400 MHz, DMSO-$d_6$) δ 7.78 (s, 1H), 7.06 (s, 1H), 6.92 (d, J=12.5 Hz, 1H), 6.68 (d, J=7.5 Hz, 1H), 5.64 (s, 2H), 5.45 (s, 1H), 5.36 (s, 2H), 5.31 (s, 1H), 1.52 (s, 12H).

Embodiment 2: Preparation of the Crystal Form a of the Compound Represented by Formula (I)

100 mg of the compound represented by formula (I) was added into a glass vial and added with 1 mL of MeOH, and the solution was clarified. After a magnetic stirrer was added thereto and the mixture was left at room temperature. The above sample was stirred at 50° C. for 48 hours, then cooled to 25° C. and stirred for 4 hours. The dissolved sample was naturally volatilized to dryness to obtain the crystal form A of the compound represented by formula (I).

Embodiment 3: Preparation of the Crystal Form B of the Compound Represented by Formula (I)

The compound represented by formula (I) was subjected to a TGA heating experiment to 160° C., and the sample was tested for XRPD after cooling to obtain the crystal form B of the compound represented by formula (I).

100-150 mg of the compound represented by formula (I) was respectively added to a glass vial and 1 mL of solvent was respectively added thereto as shown in Table 5 below to form a suspension. After a magnetic stirrer was added thereto and the mixture was left at room temperature, and the above sample was stirred at 50° C. for 48 hours, then cooled to 25° C. and stirred for 4 hours. The mixture was filtered and dried to obtain the crystal form B of the compound represented by formula (I).

TABLE 5

| No. | Compound mass | Solvent | Volume ratio | Crystal form |
|---|---|---|---|---|
| 1 | 150 mg | Ethanol | / | Crystal form B |
| 2 | 150 mg | Ethyl acetate | / | Crystal form B |
| 3 | 100 mg | Acetonitrile | / | Crystal form B |
| 4 | 100 mg | Methyl tert-butyl ether | / | Crystal form B |
| 5 | 150 mg | Methyl tert-butyl ether:methanol | 95:5 | Crystal form B |
| 6 | 100 mg | Methyl tert-butyl ether:ethanol | 95:5 | Crystal form B |
| 7 | 150 mg | Acetonitrile:water | 95:5 | Crystal form B |

Embodiment 4: Preparation of the Crystal Form C of the Compound Represented by Formula (I)

50 mg of the compound represented by formula (I) was added to a glass vial and added with 1 mL of n-heptane to form a suspension. After a magnetic stirrer was added thereto and the mixture was left at room temperature, and the above sample was stirred at 50° C. for 48 hours, then cooled to 25° C. and stirred for 4 hours. The mixture was filtered and dried to obtain the crystal form C of the compound represented by formula (I).

Embodiment 5: Preparation of the Crystal Form D of the Compound Represented by Formula (II)

About 50 mg of the compound represented by formula (I) was added to a 4.0 mL glass vial, then added with an appropriate amount of methanol, and filtered by centrifugation. The clarified solution was sealed with tin foil, pierced with small holes, and left to slowly evaporate at room temperature. After the evaporation was completed, the residue was transferred to a vacuum drying oven at 40° C. to dry overnight to obtain the crystal form D of the compound represented by formula (II).

Experimental Embodiment 1: In Vitro Aldehyde Capture Capacity Experiment

1. Experiment Objectives and Processes

Objectives: Xerophthalmia is caused by inflammation inside the eyes, wherein the inflammation may produce aldehydes in the body that will accelerate the inflammation symptoms and worsen the xerophthalmia if not eliminated in time. In the experiment, a relatively good compound was selected according to the complexing capacity of the drug and aldehydes in vivo by simulating the in vivo environment.

Processes: Sulfobutyl-B-cyclodextrin (310 mg) was dissolved in a phosphate buffer (1.25 mL) to prepare a solution.

Nonanal (5.0 mg, 32 μmol, 1.0 eq) and triolein (300 mg) were added to a reaction flask at room temperature, after the prepared solution described above was added thereto, linoleic acid (300 mg) was added thereto, and finally a dimethyl sulfoxide (0.15 mL) solution containing the compound (32 μmol, 1.0 eq) of the present disclosure was added thereto; the reaction solution was reacted at 20-23° C.

The reaction solution was reacted under stirring for 10 min, 100 min, 200 min, and 300 min respectively, and sampled for high performance liquid chromatography after the solution was stratified after standing for 2 min.

Sampling method: 25 μL of an upper emulsified layer and 50 μL of a lower aqueous layer were sampled by a pipette, and samples were diluted with 1 mL of methanol.

2. Experimental Results

Figure 4:
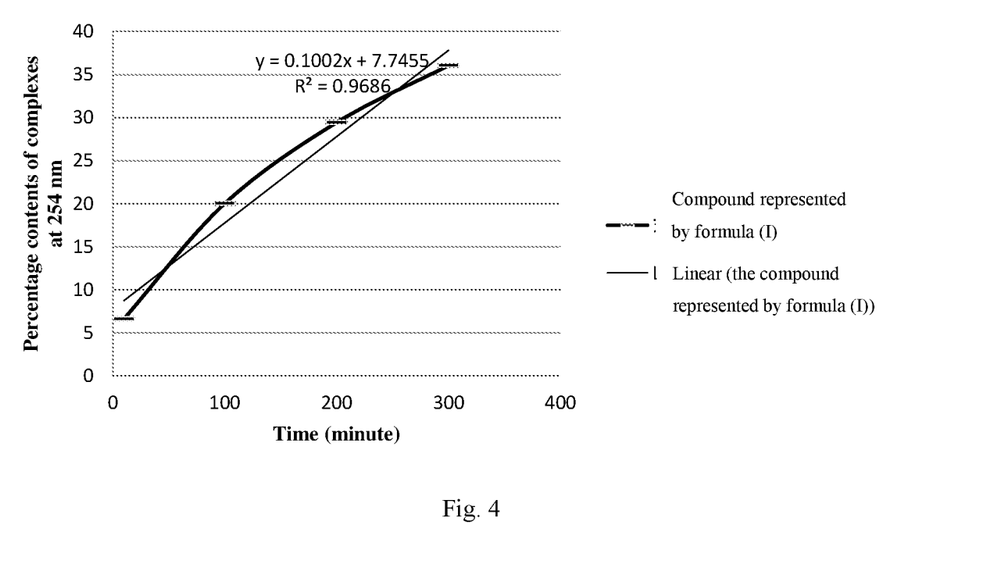
FIG. 4 is the experimental results of in vitro aldehyde trapping capacity.

The ultraviolet absorption of the nonanal was relatively weak at 254 nm, so the nonanal had a relatively small overall effect on the content of complexes. Therefore, the percentage contents of complexes at 254 nm under high performance liquid chromatography were compared to observe the ability of compounds to capture and complex aldehydes, as shown in FIG. 4 and Table 6:

TABLE 6

Statistics of test results of aldehyde capture capacity of the compound

| Compound No. | Linear Equation | Slope | Regression Coefficient $R^2$ | Area under the curve AUC (min.conversion) |
|---|---|---|---|---|
| Compound represented by formula (I) | y = 0.1002x + 7.7455 | 0.1002 | $R^2$ = 0.9686 | 6944 |

The HPLC analysis method is detailed in Table 7, which is XBRIGE 2.5 μm, 3.0*100 mm 5-80CD_XBEH_12 min_0.8.1cm

TABLE 7

| Chromatographic column | XBridge BEH C18 3.0 * 100 mm, 2.5 μm |
|---|---|
| Detection wavelength | 220, 254 nm |
| Column temperature | 40° C. |
| Flow rate | 0.8 mL/min |
| Injection volume | 1 μL |
| Mobile phase | A: 0.02% ammonia aqueous solution |
| | B: Acetonitrile |

| Gradient elution | Time (min) | A % | B % |
|---|---|---|---|
| | 0.01 | 95 | 5 |
| | 6.00 | 40 | 60 |
| | 9.00 | 20 | 80 |
| | 12.00 | 20 | 80 |

After 300 min of reaction, retention times of 6.689 min, 6.787 min, 6.966 min, and 7.102 min were absorption peaks of products complexed with monomolecular aldehyde; retention times of 8.905 min, 9.010 min, and 9.075 min were absorption peaks of products complexed with bimolecular aldehyde.

The percentage content of the specific complex at 254 nm was calculated as the sum of the percentage contents of the absorption peaks for the retention time described above, i.e., (1.839+1.715+14.993+13.029)%+(1.004+2.212+1.247)%=36.039%

The specific HPLC data of the percentage contents of complexes of the compounds of the present disclosure are as shown in Table 8 below:

TABLE 8

| | Time (min) | | | |
|---|---|---|---|---|
| Compound | 10 | 100 | 200 | 300 |
| Compound represented by formula (I) | 6.634 | 20.013 | 29.424 | 36.039 |

Conclusion: The compound represented by formula (I) has a very significant ability and speed of complexing aldehydes.

Experimental Embodiment 2: In Vitro Evaluation

Experimental objective: To study the inhibitory effect of compounds on human liver microsomal cytochrome P450.

Experimental processes: In the study on inhibition of the compounds on the human liver microsomal cytochrome P450 (CYP1A2, CYP2C9, CYP2C19, CYP2D6 and CYP3A4), pooled human liver microsomes were selected as a CYP450 enzyme source. The compounds of different concentrations (10, 5, 1.5, 0.5, 0.15, 0.05, 0.015 mM) were incubated with probe substrates (wherein two substrates were used in CYP3A4) and cofactors (NADPH) of 5 CYP enzymes to determine the $IC_{50}$ value of compound for the inhibition of each CYP enzyme. The experimental results are as shown in Table 9 below:

TABLE 9

Experimental results of inhibitory effect of compounds of the present disclosure on human liver microsomal cytochrome P450 isoenzymes

| Compound No. | CYP1A2/CYP2C9/CYP2C19/CYP2D6/CYP3A4 (μM) |
|---|---|
| Compound represented by formula (I) | >50/>50/>50/>50/>50 |

Conclusion: The compound represented by formula (I) has a high safety and low possibility of drug interaction.

Experimental Embodiment 3: Pharmacokinetic Evaluation of the Compound

I.

Experimental objective: To study pharmacokinetics of the compound in Beagle dogs Experimental material: Beagle dogs (male, 8-11 kg, greater than or equal to 6 months, Marshall)

Experimental Processes:

Pharmacokinetic characteristics of the compound were tested by intravenous injection in rodents according to the standard protocol. In the experiment, the candidate compound was prepared as a clear solution, and was administrating to Beagle dogs at 1 mg/kg by single intravenous injection. A vehicle for intravenous injection was a 10% hydroxypropyl β-cyclodextrin aqueous solution. Whole blood samples were collected at 0.033, 0.083, 0.25, 0.5, 1, 2, 4, 8, 12, and 24 hours, respectively, centrifuged at 3000 r for 10 min, and the supernatant was separated to obtain plasma samples. 20 μL of plasma samples were mixed with 400 μL of acetonitrile solution containing internal standard to precipitate protein, and the mixture was centrifuged, then 2 μL of the supernatant was injected. Plasma concentrations were quantitatively analyzed by LC-MS/MS analysis method, and pharmacokinetic parameters, such as clearance rate, half-life, and area under the concentration-time curve, were calculated.

The experimental results are as shown in Table 10:

TABLE 10

Pharmacokinetic test results

| Test Sample | Clearance rate (mL/min/kg) | Half-life $T_{1/2}$ (h) | Area under the concentration-time curve AUC (nM · hr) |
|---|---|---|---|
| Compound represented by formula (I) | 11.3 | 2.94 | 4672 |

Conclusion: The compound represented by formula (I) has a high clearance rate, a moderate half-life and good pharmacokinetic characteristics.

II.

Experimental objective: To study pharmacokinetics of the compound in cynomolgus monkeys Experimental material: Cynomolgus monkeys (male, 2.5-4 kg, greater than or equal to 2 years, Hainan Jingang)

Experimental Procedures:

Pharmacokinetic characteristics of the compound were tested by intravenous injection in monkeys according to the standard protocol. In the experiment, the candidate compound was prepared as a clear solution, and was administrating to cynomolgus monkeys at 1 mg/kg by single intravenous injection. A vehicle for intravenous injection was a 10% hydroxypropyl β-cyclodextrin aqueous solution. Whole blood samples were collected at 0.033, 0.083, 0.25, 0.5, 1, 2, 4, 8, 12, and 24 hours, centrifuged at 3000 r for 10 min, and the supernatant was separated to obtain plasma samples. 20 μL of plasma samples were mixed with 400 μL of acetonitrile solution containing internal standard to precipitate protein, and the mixture was centrifuged, then 2 μL of the supernatant was injected. Plasma concentrations were quantitatively analyzed by LC-MS/MS analysis method, and pharmacokinetic parameters, such as clearance rate, half-life, and area under the concentration-time curve, were calculated.

The experimental results are as shown in Table 11:

TABLE 11

Pharmacokinetic test results

| Test Sample | Clearance rate (mL/min/kg) | Half-life $T_{1/2}$ (hr) | Area under the concentration-time curve AUC (nM · hr) |
|---|---|---|---|
| Compound represented by formula (I) | 4.6 | 3.91 | 13016 |

Conclusion: The compound represented by formula (I) has a high clearance rate, a moderate half-life and good pharmacokinetic characteristics.

Experimental Embodiment 4: Study on Pharmacokinetic Properties In Vivo

Experimental objective: To study the ratio of corneal to plasma drug concentration after eye drop administration in rats Experimental material: Male SD rats, 200-300 g, 7-9 weeks old, Shanghai Lingchang Experimental processes: The candidate compound was prepared as a clear solution, and administrating to SD rats by eye drop administration. The vehicle for eye drops was 10% hydroxypropyl β-cyclodextrin aqueous solution, and the drug concentration in the eye drops was 5 mg/mL. Corneal and whole blood samples were collected at 1 and 4 hours, respectively. Corneal was homogenized using 15 mM phosphate buffer (PBS): MeOH (2:1, v:v) buffer, then the whole blood samples were centrifuged at 3000 r for 10 min, and the supernatant plasma samples were separated. 20 μL of the plasma samples and homogenate samples were respectively mixed with 400 μL of acetonitrile solution containing internal standard to precipitate protein, and the mixture was centrifuged, then 2 μL of the supernatant was injected. The plasma concentrations were quantitatively analyzed by LC-MS/MS analysis method; the drug concentrations in the cornea and plasma were measured respectively according to different time points, and the ratio of corneal/plasma was calculated.

Experimental results are as shown in Table 12:

TABLE 12

Pharmacokinetic test results

| Test Sample | Time | Corneal concentration (nM) | Plasma concentration (nM) | Corneal concentration/ plasma concentration C/P ratio |
|---|---|---|---|---|
| Compound represented by formula (I) | 1 h | 2447 | 172 | 11.8 |
| | 4 h | 330 | 24.4 | 12.4 |

Conclusion: As shown in the DMPK test, it can be seen that the compound represented by formula (I) can enter the cornea by eye drop administration to show the efficacy. The ratio of cornea/plasma of the compound represented by formula (I) is relatively high (above 10). The efficacy has good targeting property on the cornea.

Experimental Embodiment 5: In Vivo Efficacy Evaluation

Experimental Objectives:

Subcutaneous injection of scopolamine may induce the xerophthalmia in mice. Decreased tear secretion and inflammatory infiltration can be observed by tear tests and corneal fluorescence staining scores. Furthermore, it is possible to predict whether the model can reach the expected severity at the beginning of the modeling.

Experimental Design:

Twenty animals were selected from 25 female C57BL/6J mice and randomized into 4 groups by body weight via Provantis or Excel, 4 animals per group, and the grouping might also refer to the results of the tear test and the corneal fluorescence staining score of each animal prior to the experiment.

The mice were injected subcutaneously with scopolamine hydrobromide (3±0.5 h) for 4 times daily at 0.1 mL/animal/time on Day 1 to Day 12 of the experiment to establish xerophthalmia models in the mice.

On Day 1 to Day 13 of the experiment, animals were administrated by binocular eye drops for 4 times daily (3±0.5 h) at 3 μL/eye (on Day 13, animals in Group 1 were not administrated). Each subcutaneous injection of the scopolamine hydrobromide was be administrated prior to eye drop administration (except examinations on Day 7 and Day 12).

Tear tests and corneal fluorescence staining scores were performed on all experimental animals on Day 7 and Day 12 prior to modeling.

Criteria for corneal fluorescence staining scores: The cornea of an animal was divided into 5 regions, respectively being upper, lower, nasal, temporal and central regions, and each region was 0-3 points, and each region was scored. The monocular score was the sum of scores of the 5 regions. 0: no staining; 1: slight staining, punctate staining with less than 5 spots; 2: moderate staining, punctate staining but no plaque staining; 3: severe staining, marked fluorescent plaques.

Figure 5:
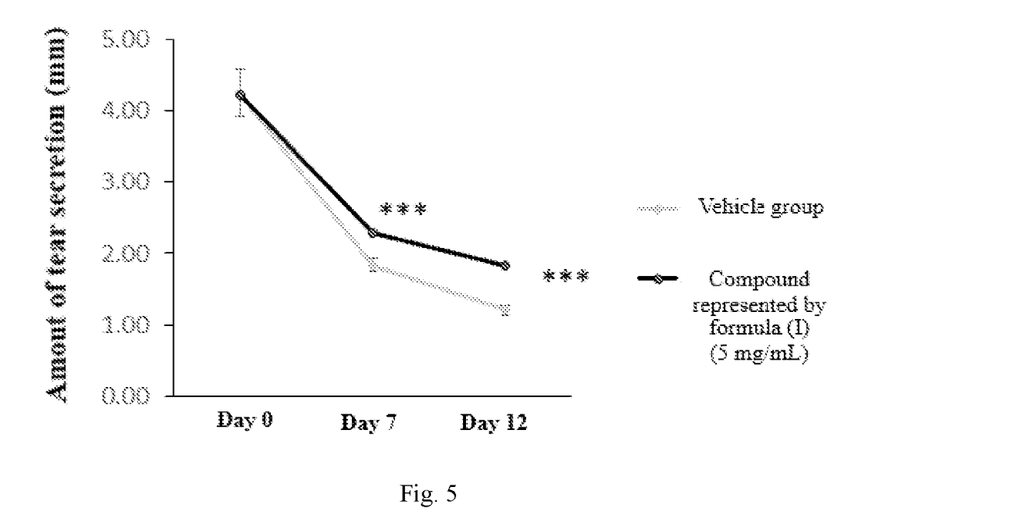
FIG. 5 is the amount of tear secretion results of an efficacy experiment on xerophthalmia in mice.
Figure 6:
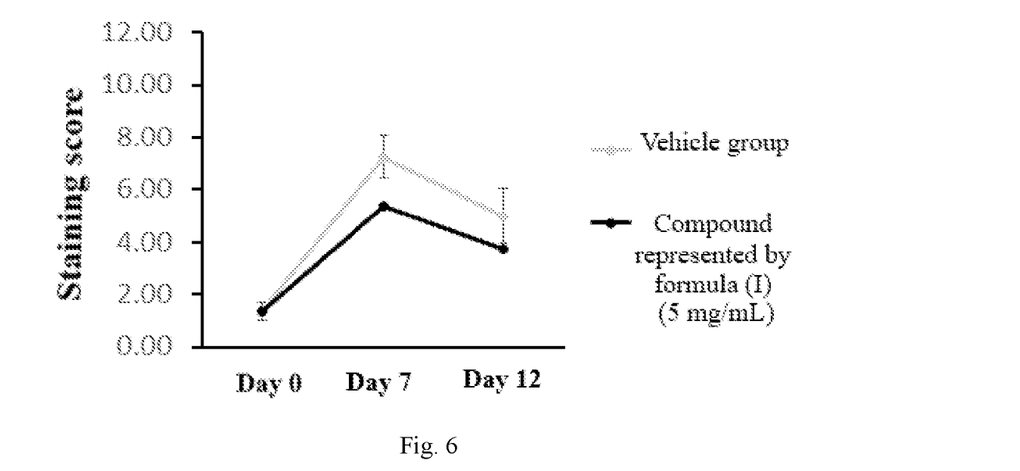
FIG. 6 is the fluorescence staining results of cornea of an efficacy experiment on xerophthalmia in mice.

The tear test was performed 30 min after the second administrating on Day 7 and Day 12 for all experimental animals, and the corneal fluorescent staining score examination of Day 7 and Day 12 for all experimental animals was performed 30 minutes after the third administration. The experimental conditions are as shown in Table 13:

Experimental results: See FIG. 5 and FIG. 6 (Note: * in the attached drawings indicates P≤0.5,  indicates P≤0.01, and * indicates P≤0.001).

Conclusion: Under the conditions of the experiment, it can be seen that the compound represented by formula (I) can improve tear secretion and corneal inflammation, showing the efficacy of improving the xerophthalmia.

What is claimed is:

1. A crystal form A of a compound represented by formula (I), wherein the crystal form A has an X-ray powder diffraction pattern comprising characteristic diffraction peaks at the following 2θ angles: 7.03±0.20°, 16.36±0.20°, and 21.23±0.20°;

(I)

2. The crystal form A according to claim 1, wherein the X-ray powder diffraction pattern thereof comprises characteristic diffraction peaks at the following 2θ angles: 7.03±0.20°, 8.20±0.20°, 16.36±0.20°, 17.73±0.20°, 20.69±0.20°, 21.23±0.20°, 22.51±0.20°, and 28.36±0.20°.

3. The crystal form A according to claim 2, wherein the X-ray powder diffraction pattern thereof comprises characteristic diffraction peaks at the following 2θ angles: 7.03±0.20°, 8.20±0.20°, 14.16±0.20°, 16.36±0.20°, 17.73±0.20°, 19.42±0.20°, 20.69±0.20°, 21.23±0.20°, 22.51±0.20°, and 28.36±0.20°.

4. The crystal form A according to claim 3, wherein the X-ray powder diffraction pattern thereof comprises characteristic diffraction peaks at the following 2θ angles: 7.03°, 8.20°, 9.19°, 12.53°, 13.09°, 14.16°, 15.78°, 16.36°, 17.73°, 18.46°, 19.42°, 20.15°, 20.69°, 21.23°, 22.51°, 23.45°, 24.02°, 24.86°, 27.36°, 28.36°, 31.36°, 32.41°, and 38.61°.

5. The crystal form A according to claim 4, wherein the crystal form A has an XRPD pattern as shown in FIG. 1.

6. A crystal form B of the compound represented by formula (I), wherein the crystal form B has an X-ray powder diffraction pattern comprising characteristic diffraction peaks at the following 2θ angles: 14.28±0.20°, 14.78±0.20°, and 20.18±0.20°;

TABLE 13

Pharmacodynamic experimental scheme of subcutaneous injection of scopolamine in mice

| Group | Number of animals (Female) | Modeling | Therapy Both eyes | Method of Administration |
|---|---|---|---|---|
| Vehicle | 4 | Subcutaneous injection of scopolamine 4 times/day, 12 days in total (5 mg/mL, 0.1 mL/time, 3 ± 0.5 h) | Vehicle 0.5% | Eye drop administration 3 μL/eye 4 times/day (3 ± 0.5 h) |
| Compound represented by formula (I) | 4 | | | |

(I)

7. The crystal form B according to claim 6, wherein the X-ray powder diffraction pattern thereof comprises characteristic diffraction peaks at the following 2θ angles: 10.08±0.20°, 12.60±0.20°, 14.28±0.20°, 14.78±0.20°, 20.18±0.20°, 21.32±0.20°, 26.08±0.20°, and 27.69±0.20°.

8. The crystal form B according to claim 7, wherein the X-ray powder diffraction pattern thereof comprises characteristic diffraction peaks at the following 2θ angles: 10.08±0.20°, 12.60±0.20°, 14.28±0.20°, 14.78±0.20°, 20.18±0.20°, 21.32±0.20°, 25.26±0.20°, 26.08±0.20°, 27.69±0.20°, and 29.63±0.20°.

9. The crystal form B according to claim 8, wherein the X-ray powder diffraction pattern thereof comprises characteristic diffraction peaks at the following 2θ angles: 8.09°, 10.08°, 12.60°, 14.28°, 14.78°, 15.13°, 16.08°, 16.38°, 17.51°, 18.25°, 20.18°, 20.56°, 21.12°, 21.32°, 22.65°, 23.85°, 24.15°, 24.77°, 25.26°, 26.08°, 26.34°, 26.64°, 27.69°, 28.94°, 29.12°, 29.63°, 30.43°, 32.16°, 32.53°, 33.34°, 33.74°, 34.74°, 35.13°, 36.20°, 37.95°, and 38.24°.

10. The crystal form B according to claim 9, wherein the crystal form B has an XRPD pattern as shown in FIG. 2.

11. The crystal form B according to claim 6, wherein the crystal form B has a differential scanning calorimetry curve with a peak value of an endothermic peak at 183.85±3.0° C.

12. The crystal form B according to claim 11, wherein the crystal form B has a DSC pattern as shown in FIG. 7.

13. The crystal form B according to claim 6, wherein the crystal form B has a thermogravimetric analysis curve with a weight loss of 0.339% occurred at 172.58° C.±3.0° C.

14. The crystal form B according to claim 13, wherein the crystal form B has a TGA pattern as shown in FIG. 7.

\* \* \* \* \*